United States Patent [19]

Hobbs et al.

[11] 4,453,226

[45] Jun. 5, 1984

[54] METHOD AND APPARATUS FOR PARTICLE SIZE DETERMINATION IN A HOST MATERIAL

[75] Inventors: Robert H. Hobbs, Vernon; Peter R. Solomon, West Hartford, both of Conn.

[73] Assignee: United Technologies Corporation, Hartford, Conn.

[21] Appl. No.: 283,599

[22] Filed: Jul. 15, 1981

[51] Int. Cl.³ ............................................ G01N 27/00
[52] U.S. Cl. ..................................... 364/555; 377/11; 324/71.4
[58] Field of Search ................. 364/554, 555; 377/10, 377/11; 324/71.4; 250/310, 399; 378/86, 88, 89

[56] References Cited

U.S. PATENT DOCUMENTS

| | | | |
|---|---|---|---|
| 3,919,050 | 11/1975 | Curby | 377/11 |
| 3,982,183 | 9/1976 | Collineau et al. | 377/11 |
| 4,037,101 | 7/1977 | Okumura et al. | 250/310 |
| 4,090,074 | 5/1978 | Watt et al. | 378/88 |
| 4,318,180 | 3/1982 | Lundquist et al. | 364/555 |

OTHER PUBLICATIONS

"New Method for Sulphur Concentration Measurements in Coal and Char" by *Solomon et al.*, Published in Fuel, vol. 56, Oct. 1977, pp. 393–396.

*Primary Examiner*—Gary Chin
*Attorney, Agent, or Firm*—Stephen A. Schneeberger

[57] ABSTRACT

A method and apparatus for determining the size distribution of certain particles, of a particular composition, such as iron sulfide (pyrites), in a sample of host material, such as coal. Data representative of the amount of at least one predetermined elemental constituent of the particles is obtained for each of numerous similarly-sized subsamples of the sample. The "constituent amount" data for each subsample is sorted into bins, each representative of a respective constituent amount range in a series of constituent amount ranges. Respective scaler representations of the fraction of the constituent amounts, represented by each bin range, are provided to yield an approximate representation of the distribution function of the amounts of the constituent in the subsamples of the coal. Those scaler representations collectively may provide a histogram. A selected multi-parameter distribution function, such as joint distribution function using both Gaussian and Poisson distributions, is fitted to the peaks of the binned grouping of representations forming the histogram, as by a least squares fitting technique, to obtain a best fit. The resulting values for two or more of the parameters of that function characterize the underlying size distribution of the certain particles in the sample. Three parameters include mean particle number density in the subsamples, mean particle radius which is a function of the mean normalized strength of the microprobe signal, and the variance in the radius.

13 Claims, 4 Drawing Figures

METHOD AND APPARATUS FOR PARTICLE SIZE DETERMINATION IN A HOST MATERIAL

DESCRIPTION

1. Technical Field

The invention relates to the analysis of minerals and more particularly to the determination of the size distribution of particles of a particular composition in a host material. More particularly still, the invention relates to a method and apparatus for determining the particle size distribution of particles, such as pyrite (iron sulfide), in samples of a host material, such as coal.

2. Background Art

There exist various instances when it is desirable to be able to make a determination of the size and/or the size distribution of certain particles contained within a host material. The determination of pyrite size distribution in coal provides a particularly good example of this need. Present limitations on the acceptable levels for $SO_2$ and $NO_x$ emissions from powerplants make the direct burning of 80% of U.S. eastern and midwestern coals unlawful in the United States. Further restrictions on other emissions from major and minor mineral componets may further restrict the use of coal.

The development and implementation of coal cleaning procedures requires extensive characterization of feed coals and the products of the cleaning process, but many of the techniques for this characterization are cumbersome and inaccurate. For instance, research by the U.S. Bureau of Mines has demonstrated that the extent of pyrite removal from coal by mechanical cleaning procedures can be predicted from the pyrite size distribution in the coal. Determination of the pyrite size distribution is typically done by visual microscopic examination of polished coal samples. This procedure is time-consuming and its accuracy depends on the observer. Some improvements in this procedure have been attempted by the automation of the optical examination and, while such automated procedures cut down on the time for analysis substantially, careful sample preparation is still required and certain disadvantages remain including lack of accuracy for small pyrite particles.

Recently, a method was developed by United Technologies Corporation, assignee of the present invention, for measuring sulfur concentration in coal and char. That method, referred to by the acronym MASC (Microprobe Analysis of Sulfur in Coal), reduces or eliminates many of the deficiencies of the prior art in determining the organic sulfur concentration and the stoichiometry of iron sulfide (pyrite) compounds in coals and chars. Briefly, that method is based on the differences in the spatial distribution of mineral sulfur (clustered distribution) and organic sulfur (relatively uniform distribution). The method uses a scanning electron microprobe to measure the spatial distribution of a number of elements of interest, including iron and sulfur. Electrons from the microprobe cause the elemental constituents of the coal to radiate X-rays at wavelengths characteristic of each element. The X-ray intensities for a large number of subsamples are measured. Considering just X-rays emitted by iron and sulfur as a first approximation, a plot of the intensities of these X-rays in a scatter plot of iron versus sulfur reveals that the data lie along a line. The intercept of that line on the sulfur axis represents sulfur which has no iron, i.e., non-pyrite sulfur; and the line has a slope which is indicative of the stoichiometry of the pyrite. In addition, the average of the iron data, when properly calibrated, represents the concentration of pyrite present. Reference may be made to an article entitled "New Method for Sulfur Concentration Measurements in Coal and Char" appearing in FUEL, 1977, Vol. 56, October, published by I.P.C. Science and Technology Press Limited, for additional details concerning the MASC procedure.

The data developed by the above-mentioned MASC procedure has been used for the determination of significant information regarding the chemical composition and lesser information regarding the concentration of various particles, and particularly pyrites, present in a sample of coal. However, no technique existed for using such data to determine the size and/or size distribution of various particles in those coal samples. Moreover, knowledge of the size distribution of these particles enables a more accurate determination of concentration in the sample.

Accordingly, it is a principal object of the present invention to provide an improved method and apparatus for determining the size of certain particles in a host material, such as coal. Included within this object is the provision of a method and apparatus for determining pyrite size distributions in coal samples. Further included within this object is the accomplishment of such size distribution determination in a relatively rapid and efficient manner.

It is a further object of the present invention to provide a method and apparatus for rapidly and accurately determining the distribution of pyrite size in coal. Included within this object is the further determination of the average number of pyrite particles per sample.

In accordance with the present invention, there is provided apparatus and a method for determining the size distribution of certain particles of a particular composition in a sample of host material, such as coal, utilizing data representative of the amount of at least one predetermined elemental constituent of the particles for each of numerous similarly sizes subsamples of the sample. The data representative of the amount of the constituent for each subsample is sorted into a plurality of data bins, each bin being representative of a respective constituent amount range in a series of successsive constituent amount ranges. Respective scaler representations of the fraction of the constituent amounts, represented by each bin range, are then provided. This provides an approximate representation of the distribution function of the amounts of the constituent occurring in the subsamples of the coal. Those scaler representations collectively provide a histogram if plotted graphically. A selected multi-parameter distribution function is fitted to the peaks of the binned grouping of representations forming the histogram to obtain a best fit. The resulting values for two or more of the parameters of that function characterize the underlying size distribution of the certain particles in the sample. The distribution function is preferably a joint distribution function using a Gaussian distribution or the like and a Poisson distribution. Three parameters of that function utilized for determining particle size distribution include mean particle number density in the subsamples, $\bar{n}$; mean particle radius, $\bar{r}$, which is a function of the mean normalized signal strength, $\bar{s}$; and the variance or spread in this radius, which is a function of the variance of the signal spread, v.

In a preferred application, the particles of interest are iron sulfide, or pyrites, and the elemental constituent measured may be either iron or sulfur, or both. The number of subsamples obtained generally exceeds 300 and the number of bins into which the data is placed typically is 10 or more. The size of each subsample is chosen to normally include several particles. A least squares fitting technique is preferably employed for fitting the distribution function to the data histogram.

BEST MODE FOR CARRYING OUT THE INVENTION

The invention determines the particle size distribution of certain particles in a sample of a host material, such as coal, by analyzing the stimulated X-ray intensities detected for one or more constituents of a particle for each of numerous subsamples of the coal sample. This technique is termed MAPS (Microprobe Analysis of Particle Sizes) for convenience. By way of example rather than limitation, the host material under consideration is coal and the particles under consideration may typically be iron sulfide or pyrites. Moreover, the constituent analyzed may be iron alone, sulfur alone or iron and sulfur jointly. For purposes of this example, detailed consideration is limited to an analysis of iron. It should be understood, however, that an analysis of iron alone is sufficient for the determination of pyrite particle size distribution. If sulfur is chosen instead, it will be necessary to determine the stoichiometry of the iron sulfide by the aforementioned MASC process because the sulfur may appear in several chemical forms. In a typical situation, because respective X-ray intensity signals for both iron and sulfur are obtained for each of numerous subsamples to practice the MASC process, it will be convenient to utilize both sets of data to refine the MAPS procedure described below.

Figure 1:
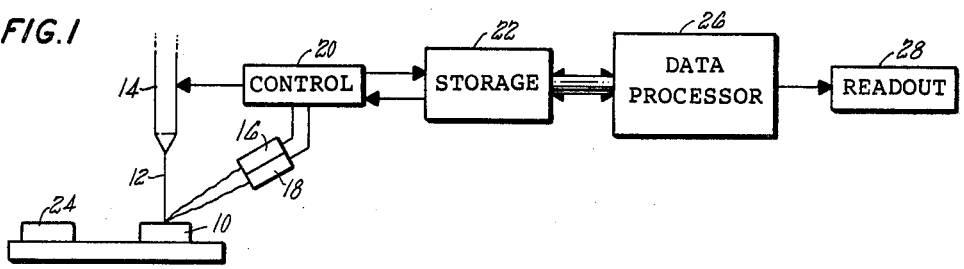
FIG. 1 is a block diagram of the apparatus utilized in the particle size distribution determination of the invention.
Figure 2:
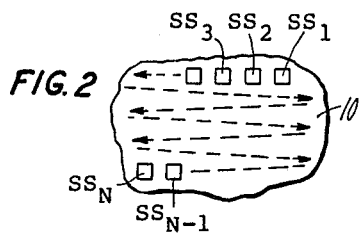
FIG. 2 is an enlarged diagrammatic view of a coal sample illustrating the numerous successive subsample scan locations thereon.

Referring to FIGS. 1 and 2, a pelletized sample of coal 10 is exposed to an electron beam 12 from cathode 14. The coal pellet sample 10 is comprised of finely ground coal, i.e. 40 mesh, which is pressed into the pellet form. The beam 12 is capable of being focused to a desired size between a few microns and several hundred microns. Two curved crystal-focusing X-ray spectrometers 16 and 18 allow simultaneous measurements of sulfur and iron X-ray emission intensities respectively. This system may conveniently be provided by a Camebax scanning electron microprobe. The microprobe is operated by an automated control system 20 which may be a suitably programmed microcomputer. Control system 20 focuses beam 12 on a particular area, or subsample SS, of sample 10; records the resulting sulfur and iron X-ray intensity data from that subsample SS in a suitable storage medium 22, as for instance a magnetic floppy disk, tape or the like; and moves the sample 10 relative to beam 12 and crystal spectrometers 16 and 18 such that a new subsample is inspected and the data recorded. Typically the sample 10 will be moved relative to beam 12 such as to provide a raster pattern of successive subsamples, illustrated in FIG. 2. Specifically, a first subsample $SS_1$ appears at the upper right of sample 10, a next subsample $SS_2$ appears immediately to the left of $SS_1$, and so on until a sufficient number of subsamples have been viewed, as at $SS_N$. By also sampling the sulfur and iron X-ray intensities from a known pyrite standard 24, the sulfur and iron X-ray intensities from each of the subsamples $SS_1$ through $SS_N$ may be normalized or calibrated to provide the weight fraction of iron or sulfur in each subsample and ultimately stored in such form in storage medium 22.

In accordance with the invention, the beam 12 is preferably adjusted to a size which is believed or determined to include at least about two, and preferably between about four and fifteen pyrite particles within its scan perimeter. While each subsample might be made so small that only one particle is seen in each and their respective sizes very accurately determined, it is necessary to inspect a significant portion of the sample and such technique would be too slow. Instead, the present technique scans the total sample rapidly with fewer, but larger, subsamples. The number of particles in each such subsample is sufficiently small for a meaningful distribution. In a typical instance, the beam will scan or view a subsample SS having a square surface area about 100 microns on a side, although that dimension may range from less than 50 microns to more than 200 microns in other situations. The intensity of the resulting X-ray signal, S, for iron, sulfur, or for that matter any other material such as calcium, silicon, etc., at a particular subsample SS is representative of the sum of the signals, s, from that particular element for all of the particles in the subsample scan zone.

The penetration depth, d, of electron beam 12 and the absorption length of the emerging X-rays, a, are such that for relatively small particles ($2r \leq d$) the X-ray intensity is proportional to the volume of the particle, while for relatively large particles ($2r >> d$), the intensity is proportional to the cross-sectional area of the particle. Thus, for a distribution of pyrite particle sizes $g(r)$ it is possible to relate the signal, s, for an element of an individual particle to its radius, r, the depth D of the particle in the coal matrix, the efficiency of the detection process, w, by the following approximate relations, jointly designated Equation 1:

$$s \simeq \begin{cases} [we^{-D/q}] \frac{4}{3} \pi d^3 \left(\frac{r}{d}\right)^3 \\ [we^{-D/q}] \frac{1}{3} \pi d^3 \left(3\left(\frac{r}{d}\right) - 1\right) \\ [we^{-D/q}] \frac{1}{3} \pi d^3 \left(3\left(\frac{r}{d}\right)^2 - 3\left(\frac{r}{d}\right) + 1\right) \end{cases} \text{for} \begin{cases} r \leq \frac{d}{2} \\ \frac{d}{2} \leq r \leq d \\ r \geq d \end{cases}$$ (Eq. 1)

This relation assumes that the density of pyrite particles in a subsample is sufficiently low that the possible shadowing of one particle by another may be ignored. From these relations it is possible to consider a distribution, f(s), of signals from individual particles. In view of the relationship expressed in Equation 1, and because typical beam penetration depth, d, of 1-2 microns are in the same general range as typical pyrite particle sizes, although some particles may be much larger and some much smaller, further reference to the intensity of an X-ray signal, s or S, herein is intended to signify detection of an "amount" of the responding elemental constituent. Thus, the "amount" of the constituent refers to its cross-sectional area and/or to its volume as determined by the relationships of Equation 1.

Assuming the distribution f(s) of signals from individual particles to have a mean s and a variance or spread v, the distribution of signals F(S,n) expected from a single subsample SS can be constructed utilizing a Gaussian, log normal or other distribution functions for f(s). For a scan which contains pyrite particles randomly drawn from the distribution f(s), (taken to be a Gaussian distribution for simplicity), the total signal measured for a subsample of n such particles would be distributed as:

$$F(S,n) \simeq \frac{1}{\sqrt{2\pi n v}} e^{-\frac{(S-n\bar{s})^2}{2nv}}$$ (Eq. 2)

for n>>1, and where S is the sum of the signals, $s_i$, from all the n particles in a subsample SS, $$S = \sum_{i=1}^{n} s_i$$ (Eq. 3)

Since the number of particles in the subsample should be distributed according to Poisson statistics, the measured signal distribution for a constituent of the pyrite particles summed over all possible values of n is described as the joint distribution function:

$$f(S) = \sum_{n=0}^{\infty} N(n;\bar{n}) F(S,n; \bar{s}, v)$$ (Eq. 4)

where F is defined in Eq. 2 and $$N(n;\bar{n}) = \frac{\bar{n}^n e^{-\bar{n}}}{n!}$$ (Eq. 5)

and $\bar{n}$ is the average number of particles per subsample.

The MAPS sizing procedure consists of least squares fitting the distribution f(S) to a histogram or similar arrangement of iron (and/or sulfur) X-ray intensity or amount data resulting from the scan of a large number of subsamples of the coal sample 10. The fitting procedure yields three parameters, two of which $\bar{s}$, v describe the underlying particle size distribution. The parameter $\bar{n}$ is the mean pyrite particle number per subsample. To convert the mean normalized signal strength $\bar{s}$ (mean of the distribution f(s)) to a mean radius, $\bar{r}$, of the particle size distribution, the relationships of Equation 1 are used. The normalization of the data already includes the terms in square brackets in Equation 1 as well as a factor of the area of the scan subsample. In the broader sense of the invention, the determination of values for the $\bar{s}$ (or $\bar{r}$) and the v parameters provides sufficient information for a relatively meaningful determination of particle size distribution. The determination of v indicates the spread of the distribution, or information on the range of particle sizes present in the coal.

Figure 3:
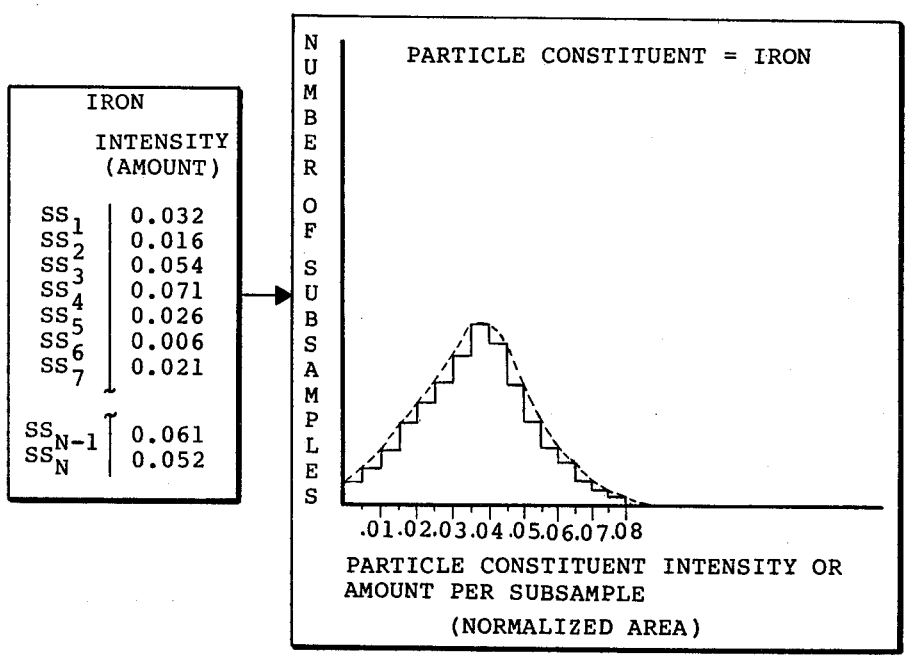
FIG. 3 is a diagrammatical illustration of an iron intensity histogram and of a distribution function fitted thereto, as determined for numerous subsamples.

In order to fit the function f(S) to the detected data, it is first necessary to sort that data into a plurality of data bins which are representative of successive adjacent ranges of particle constituent intensities or amounts. The intensity or amount signal, S, for each subsample will be assigned to an appropriate bin, and the cumulative contents of the respective bins will generally represent the function f(S) and may be plotted to form a histogram. Referring to FIG. 3 and to the flow diagram of FIG. 4, the normalized intensity data from a large number of subsamples $SS_1$–$SS_N$ previously retained in storage 22 is entered, as represented by block 30 of FIG. 4 into a data processor 26, seen in FIG. 1. That subsample data is first used for the MASC process, and then for binning and further processing in accordance with the invention. That data, as mentioned will typically include both sulfur and iron X-ray intensity signals for each subsample, however only the iron data will be discussed in detail regarding the MAPS determination. Both sets of intensity data may first be utilized for the MASC analysis, as represented by dotted block 32 in FIG. 4. That analysis determines the stoichiometry of the pyrite and may include a scatter plot of the sulfur and iron subsample data against respective axes.

Figure 4:
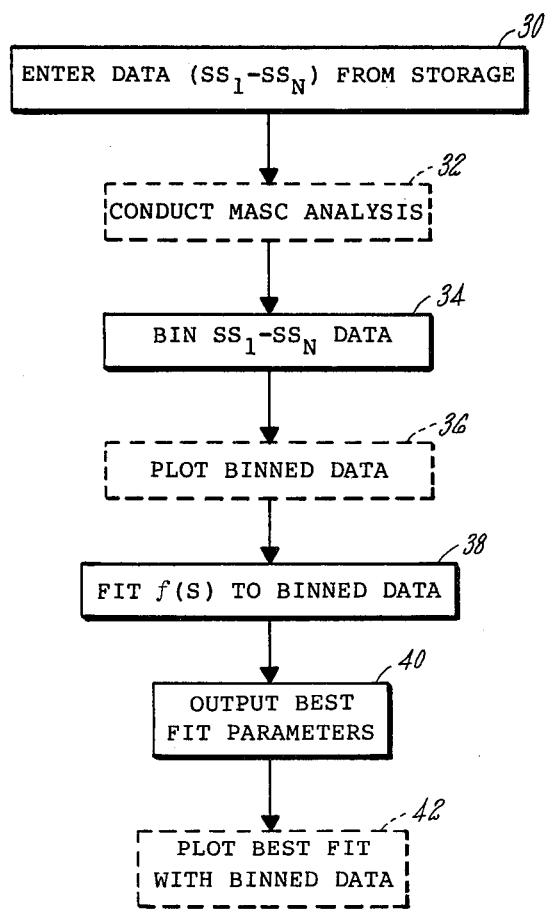
FIG. 4 is a flow diagram of the computer-implemented process for creating both the histogram and the resulting distribution curve fitted thereto, as illustrated in FIG. 3.

Then, referring to FIG. 3 and to function block 34 of FIG. 4, the iron intensity or amount values for each of the subsamples $SS_1$–$SS_N$ is assigned to an appropriate bin in the formation of a histogram. The greater the number of subsamples, combined with a relatively fine division of the intensity ranges which define the respective bins, the more readily the distribution function can be fitted to the resulting histogram. Generally, it is desirable to have at least about 300 subsamples and at least about 10 discrete bins. In the cited example, the number of subsamples is at least 300, and 16 bins have been provided. It will be understood that many more subsamples may be used, at the cost of time required to obtain those subsamples, and additional bins may also be used. Because few or none of the iron subsample intensity values, following normalization, exceed 0.080 units in the cited example, the bins of FIG. 3 are arranged to provide 16 successive bins each representative of a successive range of 0.005 intensity or amount units, extending cumulatively from zero to 0.08 units. In this embodiment, each entry of a subsample in a particular bin serves to increase the scaler value or peak of that bin by the same amount. Thus, subsamples $SS_3$ and $SS_N$ (where N might be 300) would each be placed in the bin for values from 0.050 to 0.055. This binning procedure is easily accomplished by processor 26, which is a suitably programmed general purpose digital computer, and in actual practice was a DEC PDP-6 of Digital Equipment Co.

Upon completion of the binning procedure, certain scaler values will exist for the peak or sum level of each bin. These scaler values may then be used directly by processor 26 to numerically define or quantify the distribution of the subsample data to which the distribution function will be fit. Those values may also be used for the graphical or visual presentation of the histogram depicted in FIG. 3 and as represented by the optional dotted block 36 of FIG. 4. The visual plot of the histogram may be presented on a suitable readout device 28 shown in FIG. 3, as for instance a cathode ray tube, a paper printer, or the like.

Following the binning of the iron (and/or sulfur) subsample amount data, the appropriate multi-parameter distribution function is fitted to that binned data and more specifically, is fitted to the peak or sum values of the scaler representations entered in the respective bins. In the present embodiment, the preselected distribution function comprises the joint distribution function set forth in Equation 4 above. The fitting of that function to the binned data is represented in FIG. 4 by block 38 and is accomplished by any suitable fitting technique such as a least squares fitting technique which is included in the programmed control of processor 26.

Typically the function fitting operation of the procedure involves a first step of estimating values for the various parameters of the function, determining the $f(S)$ for each bin using the estimated parameter values, plotting the resulting per-bin values of $f(S)$ for comparison with the data within the respective bins and either utilizing the estimated parameter values for the least squares fitting if the estimated values are within some predetermined acceptable limits or else selecting and trying new values for the parameters until acceptable.

Once acceptable estimated values for the function have been established, they are used to begin the least squares fitting operation. Least squares fitting is a technique which seeks (possibly through successive approximations) to minimize (within some limit) the value of the square of the difference between the actual peak value of data in a particular bin and the computed value for that bin using particular selected parameter values in the $f(S)$ function. This operation is conducted iteratively until an acceptable minimization occurs for the full range of the binned data, whereupon those particular values of the parameters of the $f(S)$ function are outputted via readout 28 as providing the best fit, as represented by block 40 of FIG. 4.

The parameters of interest are, as previously mentioned, $\bar{s}$, $\bar{n}$ and v. The parameter $\bar{s}$ (mean normalized signal strength) will generally require translation or conversion to a mean radius, $\bar{r}$, of the particle distribution, which conversion is easily made utilizing the relationships of Equation 1. This conversion may be made via the programming of processor 26 by utilizing the equation set of Equation 1 each time a conversion is needed. Alternatively, a lookup table, stored in electronic memory or printed out may list a seris of $\bar{r}$ values for a corresponding series of $\bar{s}$ values. In the latter instance, that table will have been determined using the relationships of Equation 1 and there may be need to interpolate between two adjacent values.

Finally, as represented in FIG. 3 and by the dotted block 42 in FIG. 4, the processor 26 may optionally plot via readout device 28 a trace of the distribution function $f(S)$ using the best fit parameters. That trace represented in dotted form in FIG. 3 is superimposed on the histogram plot of the binned data to show the correlation.

It will be understood that a similar analysis may be conducted, either alternatively or additionally, using the sulfur intensity values. In the event both sulfur and iron are used, they provide separate histograms and separate distribution fits; however, the distribution curves are generally in good agreement with one another as regards the values of the parameters $\bar{s}$, $\bar{n}$ and v. Moreover, the binned sulfur data and thus the distribution fit thereto will normally be displaced to the right of the origin relatively more than for iron due to the presence of some organic (i.e. non-pyritic) sulfur in the sample 10, the amount of said displacement having been previously determined in the MASC procedure as outlined in step 32 of FIG. 4.

It should be understood that the invention is not limited to the particular embodiments shown and described herein, but that various changes and modifications may be made without departing from the spirit and scope of this novel concept as defined by the following claims.

The attached is a listing of a program to operate the processor 26 in accordance with the teachings of the specification. It is written in the Fortran language for the DEC PDP-6 computer, and intended to be assembled according to standard procedures set out for USA Standard Fortran IV. Further, reference may be made to DEC System 10 Mathematical Languages Handbook, Second Edition, 1972.

We claim:

1. Apparatus for determining the size distribution of particles of a particular composition in a sample of host material comprising:
   means for stimulating the emission of X-ray radiation from the elemental constituents of numerous subsamples of said host material sample, said subsamples of said host material each being of substantially the same size and substantially all including at least two of said particles, each said elemental constituent emitting X-rays having a respective characteristic energy level, the magnitude of said emitted X-rays being indicative of the amount of said elemental constituent;
   means for sensing said X-rays having energy levels characteristic of at least a respective one of the elemental constituents of said particles of said particular composition for each said subsample and for providing elemental constituent amount signals indicative of the amount of a respective elemental constituent for each said subsample; and
   signal processing means responsive to said elemental constituent amount signals for sorting each said elemental constitutent amount signal as a function of the elemental constituent amount it represents and entering a unit count data signal in a respective one of a plurality of data bins each representing a respective elemental constituent amount value range, for summing in each said bin the unit count data signals accumulated in the respective said bin to provide respective sum signals and for fitting a preselected multi-parameter distribution function to the collective sum signals thereby to yield a plurality of parameters which jointly describe the underlying size distribution of said particles in said sample.

2. The apparatus of claim 1 wherein the host material is coal and said particles are iron sulfide (pyrites).

3. A method for determining the size distribution of certain particles of a particular composition in a sample of host material utilizing data signals representative of the amount of a predetermined at least one elemental constituent of said certain particles for each of numerous subsamples of said sample, said subsamples each being of substantially the same size, comprising the steps of:
preselecting the size of said subsamples such that each of substantially all of said subsamples includes at least two said particles;
sorting said constituent amount data signals into a plurality of data bins each representative of a respective constituent amount value range in a series of successive constituent amount value ranges;
providing respective signals representative of the sum of said constituent amount data signals accumulated in each said data bin, said signals representative of the sum of data signals in each said data bin collectively providing a histogram; and
fitting a preselected multi-parameter distribution function to the collective sum signals forming said histogram, the underlying size distribution of said certain particles in said sample being represented by the resulting values for at least two of the parameters of said function upon achieving a best fit within selected limits.

4. The method of claim 3 wherein said host material is coal.

5. The method of claim 3 wherein said subsamples number at least 300 and said data bins number at least 10.

6. The method of claim 5 wherein said data bins number at least 16.

7. The method of claim 3 wherein said distribution function is a joint distribution function of the general form $$f(S) = \sum_{n=o}^{\infty} N(n;\bar{n}) F(S,n;\bar{s},v)$$

in which $$N(n;\bar{n}) = \frac{n^{-n}e^{-\bar{n}}}{n!} \text{ and}$$

$$F(S,n;\bar{s},v) \simeq \frac{1}{\sqrt{2\pi n v}} e^{-\frac{(S-n\bar{s})^2}{2nv}}$$

for $n \gg 1$ and wherein $\bar{n}$ is the average number of particles per subsample, $\bar{s}$ is the mean normalized signal strength and $v$ is the spread of the distribution, and wherein the values for at least $\bar{s}$ and $v$ are representative of the underlying size distribution of said certain particles in said sample.

8. The method of claim 3 wherein said fitting step comprises least squares fitting said function to said collective sum signals.

9. The method of claim 4 wherein said certain particles are pyrites comprised of iron and sulfur and wherein said data representative of the amount of at least one elemental constituent is for iron.

10. The method of claim 9 wherein said data representative of the amount of at least one elemental constituent is for both iron and sulfur respectively.

11. The method of claim 3 wherein the size of said subsamples is selected such that the number of said particles in each of substantially all of said subsamples is in the approximate range of four to fifteen.

12. The method of claim 7 including the step of visually displaying said $\bar{s}$, $v$ and $\bar{n}$ parameters respectively.

13. The method of claim 3 including the step of visually displaying both the histogram provided by the collective sum signals and said distribution function fitted thereto.

* * * * *